Figure 1:
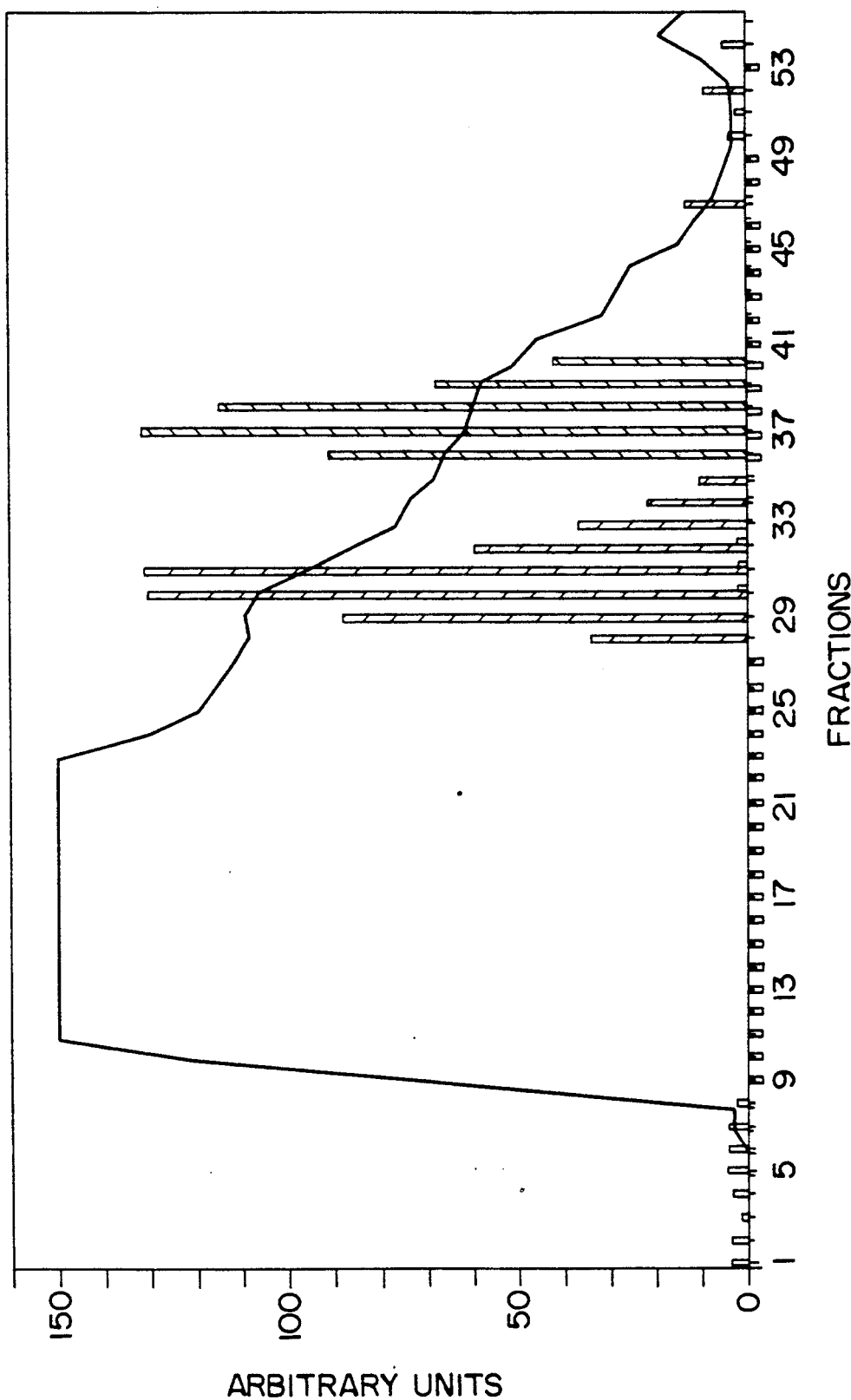

United States Patent [19]

Bertola et al.

[11] Patent Number: 5,037,751

[45] Date of Patent: Aug. 6, 1991

[54] MICROBIAL PURIFIED ESTERASES

[75] Inventors: Mauro A. Bertola; Arthur F. Marx, both of Delft; Hein S. Koger, Spaarndam; Wilhelmus J. Quax, Voorschoten; Cornelis J. van der Laken, Leiden, all of Netherlands; Gareth T. Phillips, Sittingbourne, United Kingdom; Brian W. Robertson, Sittingbourne, United Kingdom; Peter D. Watts, Sittingbourne, United Kingdom

[73] Assignee: Gist-Brocades N.V., Delft, Netherlands

[21] Appl. No.: 405,553

[22] Filed: Sep. 11, 1989

Related U.S. Application Data

[62] Division of Ser. No. 674, Jan. 6, 1987, Pat. No. 4,886,750.

[30] Foreign Application Priority Data

Jan. 7, 1986 [GB] United Kingdom ............... 8600245

[51] Int. Cl.$^5$ .......................... C12N 9/18; C12N 9/20; C12P 41/00
[52] U.S. Cl. .................................. 435/197; 435/136; 435/141; 435/198; 435/280
[58] Field of Search ............... 435/197, 198, 280, 136, 435/141

[56] References Cited

U.S. PATENT DOCUMENTS

| | | | |
|---|---|---|---|
| 4,259,446 | 3/1981 | Ando et al. | 435/199 |
| 4,394,445 | 7/1983 | Nix et al. | 435/198 |
| 4,444,886 | 4/1984 | Espers et al. | 435/197 |
| 4,565,782 | 1/1986 | Bewick | 435/280 |
| 4,568,641 | 2/1986 | Bewick | 435/280 |
| 4,629,742 | 12/1986 | Brady et al. | 521/55 |
| 4,729,953 | 3/1988 | Minai et al. | 435/280 |
| 4,762,793 | 8/1988 | Cesti et al. | 435/280 |
| 4,886,750 | 12/1989 | Bertola et al. | 435/136 |
| 4,894,336 | 1/1990 | Petzoldt et al. | 435/280 |
| 4,898,822 | 2/1990 | Asada et al. | 435/921 |

OTHER PUBLICATIONS

Gu et al., "Tetrahedron Letters", vol. 27, No. 16, pp. 1763–1766, 1986.

Primary Examiner—Herbert J. Lilling
Attorney, Agent, or Firm—Bierman and Muserlian

[57] ABSTRACT

A process for the preparation of a pharmaceutically active compound in a stereospecific form of the formula

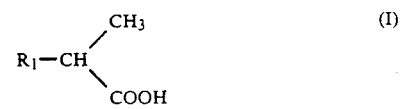

or a pharmaceutically acceptable salt or ester thereof, like an alkali metal salt or an alkaline earth metal salt or a pivaloyl ester, wherein $R_1$ represents an optionally substituted aryl group such as a phenyl or naphthyl group optionally included in a heterocyclic ring system, which is optionally substituted, or represents a heteroaromatic ring system containing in addition to carbon atoms one or more atoms selected from nitrogen, sulphur and oxygen, this ring system being optionally substituted, which comprises subjecting a compound of the formula

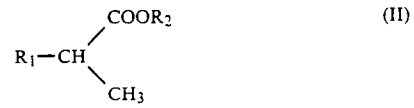

wherein $R_2$ is an ester residue and preferably an alkyl group optionally substituted, to the action of a microorganism having the ability for stereoselective hydrolysis of compound (II) into compound (I), having at least 80% by weight the S-configuration, and if desired converting compound (I) into the pharmaceutically acceptable salt or ester thereof.

5 Claims, 10 Drawing Sheets

FIG.9A    FIG.9B.

IEP

— 3.50

—4.55
—5.20

—6.55

—6.85

—7.35
—8.15
—8.45
—8.65
—9.30

2 3 4    2 3 4 1

MICROBIAL PURIFIED ESTERASES

This is a division of Ser. No. 000,674, filed Jan. 6, 1987.

The present invention relates to a process for the preparation of a pharmaceutically active compound in a stereospecific form of the formula

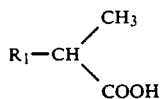     (I)

or a pharmaceutically acceptable salt or ester thereof, like an alkali metal or an alkaline earth metal salt or a pivaloyl ester, wherein $R_1$ represents an optionally substituted aryl group such as a phenyl or naphthyl group optionally included in a heterocyclic ring system, which is optionally substituted, or represents a heteroaromatic ring system containing in addition to carbon atoms, one or more atoms selected from nitrogen, sulphur and oxygen, this ring system being optionally substituted.

It is known that many biologically active compounds exist as a mixture of stereoisomers. Up to now these mixtures are frequently used as such in agricultural and pharmaceutical applications. Usually the desired biological activity resides in one stereoisomer so that in case of a two stereoisomer mixture the potency of the mixture is reduced to half. Still a major reason for the use of mixtures of stereoisomers is that the cost of separation of the stereoisomers exceeds the potential advantage of a possible increase in activity. However it is apparent that modern pharmacologists are becoming increasingly aware of other implications of the administration of mixtures wherein one of more stereoisomers have to be regarded as an impurity that may not have the desired therapeutic effect, but even may have other unwanted physiological effects including toxicity.

More particularly it has been discovered that the in vitro anti-inflammatory activity of naproxen as well as ibuprofen resides in the S-enantiomer (optically active stereoisomer) which is up to 150 times as active as its antipode as known e.g. from S. Adams et al, J.Pharm. Pharmac., 28 (1976) 256 and A. J. Hutt and J. Caldwell, Clinical Pharmacokinetics 9 (1984) 371.

S. Iriuchijima and A. Keiyu (Agric. Biol. Chem., 45 (1981) 1389, showed that selected micro-organisms are able to hydrolyse the methyl esters of naproxen and ketoprofen but with low conversions. *Aspergillus sojae* preferentially hydrolyzed the methyl ester of R-naproxen to produce naproxen having 95% by weight the R-configuration while *Mycobacterium smegmatis* preferentially hydrolyzed the methyl ester of S-ketoprofen to give ketoprofen having only 69% by weight the S-configuration.

In the German patent application DE 3345660 the production of S-Naproxen from racemic naproxen esters is described. However in this patent application the S-naproxen is not directly formed from the racemic mixture of naproxen esters, but is formed by saponification or by enzymatic hydrolysis of the S-naproxen ester, which remains in the reaction mixture after the ester of R-naproxen is enzymatically hydrolyzed and the R-naproxen formed is separated from the ester of S-naproxen.

In a recent publication (Qu-Ming et al., Tetrahedron Letters, vol. 27, no. 16 (1986) p. 17–63), an enzyme preparation from *Candida cylindracea* has been described, which is able to convert S-naproxen ester stereoselectively. Authors show that the Candida lipase, which is present in their preparation, is responsible for the naproxen ester hydrolysis. However, the specific activity of their purified lipase preparation is extremely low ($3 \times 10^{-8}$ mol/min per mg lipase under the specified conditions).

Therefore there is still a large need for a process on an industrial scale giving rise to economically attractive yields for the direct preparation of S-stereoisomers and the object of the invention is to provide such a process. As a result of extensive research and experimentation an improved selective synthesis has now surprisingly been found for preparation of particularly the S-stereoisomer of compound (I), which comprises subjecting a compound of the formula

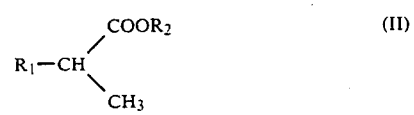     (II)

wherein $R_1$, is as defined before and $R_2$ is an ester residue and preferably an alkyl group optionally substituted, to the action of a micro-organism or substances derived therefrom, having the ability for stereoselective hydrolysis of compound (II) into compound (I), having at least 80% by weight the S-configuration, and if desired converting compound (I) into a pharmacologically acceptable salt or ester thereof.

More specifically the present invention relates to a process for predominantly producing a pharmaceutically active compound in a stereospecific S-configuration of the formula (I) or a pharmaceutically acceptable salt or ester thereof, preferably an alkali metal salt or an alkaline earth metal salt thereof, wherein $R_1$ is an optionally substituted aryl group such as a phenyl or naphthyl group, optionally included in a heterocyclic ring system, which is optionally substituted, or represents a heterocyclic ring system containing in addition to carbon atoms, one or more atoms selected from nitrogen, sulphur and oxygen, this ring system being optionally substituted, wherein $R_2$ is an alkyl group, optionally substituted, which comprises subjecting a compound of formula (II) to the action of a micro-organism having the ability for stereoselective hydrolysis of compound (II) into compound (I).

Preferably $R_2$ is a linear alkyl group of 1 to 8 carbon atoms, more preferably $R_2$ is a methyl or an ethyl group.

Preferably compound (I) is naproxen, ibuprofen, suprofen, fenoprofen, ketoprofen, benoxaprofen, carprofen, cicloprofen, pirprofen, lisiprofenum, flurbiprofen, fluprofen, clidanac, tertiprofen, hexaprofen, indoprofen, mexoprofen, pranoprofen, furaprofen, protizinic acid, tiaprofenic acid or brofezil.

More preferably according to the process of the present invention naproxen is prepared in predominantly the S-configuration.

According to a preferred embodiment, the process is carried out by selecting a proper micro-organism or substances derived therefrom in such a way that compound (I) is formed whereof at least 90% by weight is in the S-configuration.

It is another object of the invention to provide an enzyme which is at least 10 times more active than the above described *Candida cylindracea* lipase and preferably 100 times more active.

A further object of the invention is to provide a process for the preparation of compound (I) having at least 80% in the R-configuration comprising a process according to the invention, whereafter compound (I) is separated and the remaining part is hydrolyzed.

By the term "proper micro-organism" is meant for example micro-organisms belonging to the genus Bacillus, to the genus Pseudomonas, to the genus Arthrobacter, to the genus Mucor or to the genus Streptomyces.

Also micro-organisms, which have obtained the ability for stereoselective conversion of compound (II) to compound (I) through the introduction of novel genetic material are embodied by the term "proper micro-organism".

This can be accomplished by transferring the cloned gene encoding a substance responsible for the stereoselective hydrolysis, an esterase enzyme from any of the screened micro-organisms to another micro-organism, particularly to *Escherichia coli*. Other micro-organisms may be belonging to the genus Saccharomyces, Kluyveromyces, Aspergillus, Escherichia, Pseudomonas and Streptomyces. Cloned genes may be selected for their ability to encode an enzyme capable of hydrolyzing an ester preferably α-naphthyl-acetate and naproxen ester. Alternatively they may be selected by cross-hybridization with an already selected gene encoding an esterase. The latter assumption is based on the observation that related micro-organisms show homology in the DNA sequence of corresponding enzymes (Ihara et al., 1985, J. Biochem. 98, p. 95) and on our own observation that plasmid pNAPT-7 (see Example 11) exhibits cross-hybridization with chromosomal DNA derived from other Bacillus species. In addition this invention encloses a method for the introduction of multiple and/or modified gene copies encoding the esterase into a micro-organism with the profit of increasing the activity of the micro-organism, or the substances derived therefrom, in the conversion process of compound (II) into compound (I). This micro-organism may be for example *Bacillus subtilis*.

The micro-organisms may advantageously be immobilized for example with a polymer gel. This can be done with living and/or killed cells, but alternatively the esterase enzyme, may be purified to a certain extent if a higher specific activity is needed.

Therefore by the term "micro-organisms or substances derived therefrom" is meant the micro-organisms, killed or alive, extracts therefrom, optionally concentrated or purified.

More particularly the micro-organisms for the hydrolysis of the ethyl and methyl ester of naproxen [ethyl 2-(6-methoxy-2-naphthyl)propionate and methyl 2-(6-methoxy-2-naphthyl) propionate, respectively] into S-naproxen [2-(6-methoxy-2- naphthyl) propionic acid] and the hydrolysis of the ethyl and methyl ester of ibuprofen [ethyl 2-(4-isobutyl-1-phenyl) propionate and methyl 2-(4-isobutyl-1-phenyl) propionate, respectively] into S-ibuprofen [2-(4-isobutyl-1-phenyl) propionic acid] includes cultures of *Bacillus subtilis, Bacillus licheniformis* (a sample of this species is deposited with the ATCC under the accession number 11945), *Pseudomonas fluorescens, Pseudomonas putida* (a sample of this species is deposited with IFO under the accession number 12996), *Pseudomonas riboflavina* (a sample of this species is deposited with IFO under the accession number 13584), *Pseudomonas ovalis* (a sample of this species is deposited with IAM under the accession number 1049), *Pseudomonas aeruginosa* (a sample of this species is deposited with IFO under the accession number 13130), *Mucor angulimacrosporus* (a sample of this species is deposited with IAM under the accession number 6149), *Arthrobacter paraffineus* (a sample of this species is deposited with ATCC under the accession number 21218), *Strain is III-25* (a sample of this species is deposited with CBS under the accession number 666.86), Strain LK 3-4 (a sample of this species is deposited with CBS under the accession number 667.86), Strain Sp 4 (a sample of this species is deposited with CBS under the accession number 668.86), Strain Thai III 18-1 (a sample of this species is deposited with CBS under the accession number 669.86) and Strain Thai VI 12 (a sample of this species is deposited with CBS under the accession number 670.86). Advantageously, cultures of species the *Bacillus subtillus* includes cultures of species *Bacillus species Thai* 5 1-8 (a sample of this species is deposited with the CBS under the accession number 679.85), species *Bacillus species* In IV-8 (a sample of this species is deposited with the CBS under the accession number 680.85), species *Bacillus species Nap* 10-M (a sample of this species is deposited with the CBS under the accession number 805.85), species *Bacillus species Sp III*-4 (a sample of this species is deposited with the CBS under the accession number 806.85), *Bacillus subtilis* 1-85 (Yuki, S., 1967, Jpn. J. Genet. 42, p. 251), *Bacillus subtilis* 1-85/p NAPT-7 (a sample of this species is deposited with the CBS under accession number 673.86), *Bacillus subtilis* 1A-40/pNAPT-8 (a sample of this species is deposited with the CBS under the accession number 674.86) and *Bacillus subtilis* 1A-40/pNAPT-7 (a sample of this species is deposited with the CBS under the accession number 675.86). Advantageously, cultures of the *Pseudomonas fluorescens* include a culture of species *Pseudomonas species Kor I*-6 (a sample of this species is deposited with the CBS under the accession number 807.85) and *Pseudomonas fluorescens* species deposited with the IFO under the accession number 3081. IFO = Institute for Fermentation, Osaka, Japan. IAM = Institute of Applied Microbiology, University of Tokyo, Japan. According to a preferred embodiment of the process of the present invention, a micro-organism having the ability to convert compound (II) into compound (I) having at least 80% by weight the S-configuration, has to be cultured for about 0.5 to 10 days. Hereafter the cells are suspended in a liquid nutrient medium and compound (II) is subjected to the action of the cells. Alternatively the cells are killed for example suspended in a lysis medium and compound II is subjected to the action of the substances derived from the cells.

The taxonomical classification of the species is as follows:

CBS 666.86 (strain III-25) is a species of *Psuedomodonas fluorescens*

CBS 667.86 (strain LK 3-4) is a species of *Arthrobacter citreus*

CBS 668.86 (strain Sp4) is a species of *Pseudomonas fluorescens*

CBS 669.96 (strain Thai III 8-1) is a species of *Pseudomonas mendocina*

CBS 670.86 (strain Thai VI 12) is a species of *Arthrobacter citreus*

CBS 679.85 (Bacillus species Thai 1-8) is a species of *Bacillus subtilis*

CBS 680.85 (Bacillus species in IV-8) is a species of *Bacillus subtilis*

CBS 805.85 (Bacillus species Nap 10-M) is a species of *Bacillus subtilis*

CBS 806.85 (Bacillus species SP III-4) is a species of *Bacillus subtilis*

CBS 807.85 (Pseudomonas species Kor I-6) is a species of *Pseudomonas fluorescens*.

After the abovementioned cultivation for about 0.5 to 10 days the cells may be isolated from the culturing medium before suspending the cells in the liquid nutrient medium or suspending the cells in a lysis medium.

To grow the micro-organisms used for the selective hydrolysis of compound (II), ordinary culture mediums containing an assimilable carbon source (for example glucose, lactate, sucrose, etc.), a nitrogen source (for example ammonium sulphate, ammonium nitrate, ammonium chloride, etc.), with an agent for an organic nutrient source (for example yeast extract, malt extract, peptone, meat extract, etc.) and an inorganic nutrient source (for example phosphate, magnesium, potassium, zinc, iron and other metals in trace amounts) may be used.

As a preferred culture medium a Jap medium optionally enriched with one or more ingredients is used. A Jap medium of the following composition may be used: soybean flour (30 g/l), sodium nitrate (7.5 g/l) ferrous F sulphate.7$H_2O$ (0.28 g/l), sodium citrate (6 g/l) and fructose (12.5 g/l), the pH adjusted to 7.2. Before use the medium was sterilized for 20 minutes at 120° C.

Another preferred culture medium is a TSB-medium 2X, optionally enriched with one or more ingredients. A medium consisting of 60 g/l trypticase soy broth (Oxoid ®) may be used. Before use the medium was sterilized for 20 minutes at 120° C. Another preferred medium is 2×TY optionally enriched with one or more ingredients. A medium consisting of Tryptone (Difco ®) 30 g/l, Yeast extract (Difco ®) 20 g/l, NaCl 3 g/l, $(NH_4)_2HPO_4$ 1 g/l and $(NH_4)_2SO_4$ 1 g/l at pH 6.8 can be used. Before use the medium was sterilized for 30 minutes at 110° C. As a more preferred culture medium a skimmed milk medium optionally enriched with one or more ingredients is used. A skimmed milk medium of the following composition was used: 10% skimmed milk from skimmed milkpowder, which was sterilized for 30 minutes at 110° C. before use.

As enrichments to the skimmed milk medium for example 0.5% lactate or PSIII salts or combinations thereof can be used. PSIII salt medium of the following composition was used: potassiumdihydrogen phosphate (2.1 g/l), ammonium monohydrogen phosphate (1.0 g/l), ammonium sulphate (0.9 g/l), potassium chloride (0.2 g/l), sodium citrate (0.29 g/l), calcium sulphate.2-$H_2O$ (0.005 g/l), magnesium sulphate.7$H_2O$ (0.2 g/l), ammonium ferrous sulphate.6$H_2O$ (2.5 mg/l), zinc sulphate.7$H_2O$ (0.5 mg/l), manganese chloride.4$H_2O$ (0.3 mg/l), copper sulphate.5$H_2O$ (0.15 mg/l), cobalt chloride.6$H_2O$ (0.15 mg/l), ortho-boric acid (0.05 mg/l), sodium molybdate.2$H_2O$ (0.055 mg/l) and potassium iodide (0.1 mg/l), the pH was adjusted at 6.8. Before use the PSIII salt medium was sterilized for 20 minutes at 120° C.

A temperature between 0 and 45° C. and a pH between 3.5 and 9 is maintained during the growth of the micro-organisms. Preferably the micro-organisms are grown at a temperature between 20 and 37° C. and at a pH between 5 and 9.

The aerobic conditions required during the growth of the micro-organisms can be provided according to any of the well-established procedures, provided that the supply of oxygen is sufficient to meet the metabolic requirement of the micro-organisms. This is most conveniently achieved by supplying oxygen, suitably in the form of air and optionally at the same time shaking or stirring the reaction liquid. During the conversion of compound (II) into compound (I) the micro-organisms might be in a growing stage using an abovementioned ordinary culture medium or might be preserved in any system (medium or buffer) preventing degradation of enzymes.

During the conversion of compound (II) into compound (I), an ordinary culture medium may be used containing an assimilable carbon source when required (for example glucose, lactate, sucrose, etc.), a nitrogen source when required (for example ammonium sulphate, ammonium nitrate, ammonium chloride, etc.), with an agent for an organic nutrient source when required (for example yeast extract, malt extract, peptone, meat extract, etc.) and an inorganic nutrient source when required (for example phosphate, magnesium, potassium, zinc, iron and other metals in trace amounts).

Preferably, during the conversion of compound (II) into compound (I), a Jap medium (as described above) optionally enriched with one or more ingredients is used. More preferably a skimmed milk medium (as described above) optionally enriched with one or more ingredients is used.

The micro-organisms can be kept in the non-growing stage for example by exclusion of the assimilable carbon source or by exclusion of the nitrogen source. A temperature between 0 and 45° C. and a pH between 3.5 and 9 is maintained during this stage.

Preferably the micro-organisms are kept at a temperature between 20 and 37° C. and a pH between 5 and 8. The aerobic conditions required during this stage can be provided according to any of the well-established procedures, provided that the supply of oxygen is sufficient to meet the metabolic requirement of the micro-organisms. This is most conveniently achieved by supplying oxygen, suitably in the form of air and optionally, at the same time, shaking or stirring the reaction liquid. The compound (I) produced by the micro-organisms or substances derived therefrom, as mentioned above, can be recovered and purified according to any of the procedures known per se for such products.

The micro-organisms can be kept on agar slants, frozen in 50% glycerol or lyophilised. If required, precultures of these micro-organisms can be made according to any of the well-established procedures for example the micro-organisms can be incubated in bouillon or in BHI for 24 hours at 30° C. in a rotary shaker. A bouillon medium of the following composition can be used: Lab Lemco L 29 (meat extract, Oxoi ®) (9 g/l), Bactopepton (10 g/l) and sodium chloride (5 g/l), the pH adjusted to 7.6. Before use this medium was sterilized for 20 minutes at 120° C.

A BHI (brain-heart infusion) medium containing 0.037 g/l BHI (Oxoid ®), the pH adjusted to 7.0, can be used. Before use this medium was sterilized for 20 minutes at 120° C.

The enzyme responsible for the hydrolysis of S-naproxen methyl ester of *Bacillus Thai I-8* has been characterized. It has been found that the esterase activity is not related to the lipase activity present in the micro-organism. In fact the low amount of hydrolysis of the wrong isomer of naproxen, appeared to be mainly due to the contaminating lipase activity of the Bacillus strain. The purified naproxen esterase of Thai I-8 has a significant higher enantiomeric selectivity than the total cell lysate of Bacillus.

The *E. coli*/pNAPT-7 and Bacillus/pNAPT-7, both strains having a plasmid containing the Thai I-8 esterase, produce a significant amount of S-naproxen esterase. Surprisingly the protein which possesses the esterase activity as confirmed by SDS-PAGE, HPLCS-EC and isoelectricfocusing is by far out the protein with the highest concentration in the cell lysate of the micro-organisms.

Although it is known that gene cloning can improve the expression level of an enzyme, the amount of enhancement in the case of esterase is very surprising. Very often problems as incorrect folding, protein degradation and intracellular precipitation are encountered when cloning the gene for an enzyme (Harris, T.J.R., 1983, Genetic Engineering 4, Academic Press). Unexpectedly none of these problems seems to occur when cloning esterase genes.

Throughout the specification the S-specificity is defined as:

$$\frac{S \text{ (formed)}}{R \text{ (formed)} + S \text{ (formed)}}$$

The present invention will be further described with reference to the Examples, without restricting the scope of the present invention to these Examples.

EXAMPLE 1

Transformation of RS-naproxen ethyl ester into S-naproxen using *Bacillus Thai* I-8, Bacillus In IV-8, *Bacillus Nap* 10M, Bacillus Sp III-4, *Bacillus licheniformis* (ATCC 11945) and *Pseudomonas Kor* I-6

*Bacillus Thai* I-8, Bacillus In IV-8, *Bacillus Nap* 10M, Bacillus Sp III-4, *Bacillus licheniformis* (ATCC 11945) and Pseudomonas Kor I-6 were each incubated in 25 ml of 10% skimmed milk kept in 500 ml baffle flasks and incubated for 48 hours at 30° C. on a rotary shaker. After this growth period 100 mg of the ethyl ester of naproxen was dissolved in 500 mg of soyoil, kept at 110° C. for 1 hour for sterilization and added to each of the cultures. Depending on the micro-organisms 2 to 5 cultures were used. The cultures were incubated for another 24 hours at 30° C. on the rotary shaker. Thereafter the cultures were acidified with ortho-phosphoric acid to a pH value of 2 to 3, a small amount of ammonium sulphate was added and 20 ml of chloroform or ethylacetate per 25 ml medium were added for the extraction. The extracts were analyzed by TLC. For analysis with TLC silicagel plates (silicagel 60 with fluorescent indicator $F_{254}$) were eluted with chloroform +1% acetic acid to effect a separation of the ethyl ester of naproxen and naproxen. The Rf values found were, ethyl ester of naproxen 0.7 and naproxen 0.2. The organic phase was thereafter evaporated and the naproxen was purified from the resulting oil by elution with ether on a silicagel column. The results obtained are presented in Table 1.

Optical rotations were measured in a Perkin-Elmer 141 polarimeter in 1 or 10 cm pathlength cell (volume 0.5-5 ml), maintained at room temperature. Rotations were recorded at 589 nm (Sodium D-line).

The optical rotation was measured by dissolving the formed products (to a maximum of 50 mg) in 5 ml of methanol. Commercial S-naproxen (Secifarma) has an $|\alpha|$ of $+60°$

TABLE 1

Microbiol hydrolysis of ethyl 2-(6-methoxy-2-naphthyl) propionate into 2-(6-methoxy-2-naphthyl) propionic acid, conversions of substate and optical activity of product.

| Micro-organisms | Total Ester added (mg) | Ester recovered after incubation (mg) | Naproxen formed (mg) | $|\alpha|_D^{rt}$ |
|---|---|---|---|---|
| Bacillus Thai I-8 | 400 | n.d.* | 23** | +57° |
| Bacillus In IV-8 | 500 | 210 | 75 | +60° |
| Bacillus licheniformis ATCC 11945 | 200 | 53 | 32 | +52° |
| Bacillus Sp III-4 | 400 | n.d.* | 33** | +37° |
| Bacillus Nap 10M | 200 | 110 | 30 | +44° |
| Pseudomonas Kor I-6 | 200 | 93 | 25 | +43° |

*n.d. - not determined
**Quantity left after isolation.

EXAMPLE 2

The enantiomeric distribution of R and S naproxen formed by microbial hydrolysis All tests were performed with 25 ml of a medium in 100 ml baffle flasks, as described in Example 1. All media were inoculated from cultures pregrown for 24 hours in a BHI medium.

The assay was performed for 1 and for 24 hours, using approximately 20 mg of the ethyl ester of racemic naproxen dissolved in soy oil.

The extracts were analyzed by HPLC. The ester and acid were separated on a silica column (CP-Sper-Si, Chrompack). Mobile phase: isooctane/ethylacetate/formic acid (875 ml/125 ml/3.5 ml).

Flow: 1.7 ml/min. Retention times found were 3.8 minutes for the ethyl ester of naproxen and 9.0 minutes for naproxen.

The naproxen was derivatized to determine its enantiomeric purity. Naproxen samples derivatized into naphthalene methylamides were separated on a chiral DNBPG column eluted with isooctane/chloroform/methanol (900 ml/70 ml/30 ml). Flow: 2 ml/min.

Retention times for the derivatized S-naproxen and R-naproxen were 28.1 min. and 30.7 min. respectively.

Derivatization procedure: 2 ml of extract was dried under a flow of $N_2$. The dried sample was reacted with 200 µl of benzene +10 µl of thionylchloride for 10 minutes at 60° C. The reaction mixture was dried under $N_2$. 200 µl of naphthalenemethylamine, 5% dissolved in dried dichloromethane was added and the reaction was carried on for 1 hour at room temperature. The reaction mixture was 5 dried again under $N_2$ and then extracted with 2 ml of isooctane/chloroform (2:1, v/v and 2 ml of HCl, 1N). The organic phase was analyzed on HPLC. Results are presented in Table 2.

TABLE 2

The enantiomeric distribution of R and S naproxen formed by microbial hydrolysis.

| Microorganism | Incubation period (h) | S-Naproxen formed (mg/culture) | R-Naproxen formed (mg/culture) | % S-Naproxen | % R-Naproxen |
|---|---|---|---|---|---|
| Bacillus Thai I-8 | 1 | 1.26 | 0.014 | 99 | 1 |
|  | 24 | 7.14 | 0.59 | 92 | 8 |
| Bacillus In IV-8 | 1 | 0.48 | 0.008 | 98 | 2 |
|  | 24 | 4.18 | 0.40 | 91 | 9 |
| Bacillus | 1 | 0.28 | 0.014 | 95 | 5 |
| licheniformis (ATCC 11945) | 24 | 4.76 | 0.086 | 98 | 2 |
| Pseudomonas Kor I-6 | 24 | 2.8 | 0.07 | 98 | 2 |
| Bacillus Nap 10M | 24 | 1.3 | 0.01 | 99 | 1 |
| Bacillus Sp III-4 | 24 | 2.5 | 0.3 | 89 | 11 |

EXAMPLE 3

Transformation of the methyl ester of RS-naproxen into S-naproxen by the different micro-organisms All tests were performed with 25 ml of medium in 100 ml baffle flasks, as described in Examples 1 and 2. But instead of the ethyl ester of racemic naproxen, methyl ester of racemic naproxen was added to the cultures. The media were inoculated from cultures pregrown for 24 hours in a BHI-medium.

Results are presented in Table 3.

TABLE 3

| Microorganism | Naproxen formed (mg/culture) | % S | % R |
|---|---|---|---|
| Bacillus Thai I-8 | 6.9 | 96 | 4 |
| Bacillus In IV-8 | 2.0 | 90 | 10 |
| Bacillus licheniformis (ATCC 11945) | 8.6 | 98 | 2 |
| Bacillus Nap 10M | 3.2 | 99 | 1 |
| Bacillus Sp III-4 | 5.8 | 82 | 18 |

EXAMPLE 4

Transformation of the ethyl ester of S-naproxen into S-naproxen using *Bacillus Thai* I-8, Bacillus In IV-8 and *Bacillus licheniformis* (ATCC 11945)

All tests were performed with 25 ml of medium in 100 ml baffle flasks as described in Example 1. All media were inoculated from cultures pregrown for 24 hours in a BHI medium.

The quantities of the ethyl ester of S-naproxen that are hydrolyzed are presented in Table 4.

TABLE 4

Quantities of ethyl ester of S-naproxen hydrolysed in 24 hours in an enriched skimmed milk medium (PSIII and lactate were added)

| Micro-organism | Remaining ester after 24 h (mg)* | Naproxen formed (mg) |
|---|---|---|
| Bacillus Thai I-8 | 7.9 | 18.6 |
| Bacillus In IV-8 | 15.0 | 10.5 |
| Bacillus licheniformis ATCC 11945 | 11.6 | 10.2 |

*ca. 30 mg of ester was added to each culture of 25 ml

EXAMPLE 5

Transformation of the ethyl ester of racemic naproxen into S-naproxen by Bacillus species Thai I-8, grown in a fermenter Bacillus species Thai I-8 was pregrown for 24 hours in a BHI medium. Thereafter 50 ml culture was inoculated in a 10 l Eschweiler fermenter containing 10% skimmed milk medium or 10% skimmed milk enriched with PSIII salts and 5 g/l lactate.

The following fermentation conditions were used:

| | |
|---|---|
| Volume: | 5 l. medium |
| Temperature: | 30° C. |
| Stirring speed: | 500 rpm |
| Air flow: | 50 l/h |
| Antifoam: | controlled by automic addition of pluronic L 81 |
| pH: | Not regulated (kept free between pH-values of 6 and 9). |

The micro-organisms were grown for 70 hours and during that time several samples were taken and assayed for their activity towards the ethyl ester of naproxen. The assay was performed by incubating a 25 ml sample for 1 hour at 30° C. in a baffle flask to which 20 mg of the ethyl ester of racemic naproxen dissolved in soy oil was added. After this incubation period the samples were extracted, derivatized and analyzed on HPLC.

After 24 hours the dry weight of the micro-organisms and volumetric activity remained constant. The pH value of the culture increased during that period from 6.0 to 7.8 when skimmed milk was used and from 6.0 to 8.4 when the enriched skimmed milk was used.

The results are summarized in Table 5.

TABLE 5

Results of the fermentation of the Bacillus species Thai I-8 using skimmed milk and enriched skimmed milk respectively.

| | culture using skimmed milk | culture using skimmed milk enriched with PS III and lactate |
|---|---|---|
| Dry weight | 1.2–1.3 g/l | 2.5–2.6 g/l |
| Volumetric activity | 30 mg Naproxen formed/l/h | 53 mg Naproxen formed/l/h |
| Enantiomeric distribution | 96% S, 4% R | 91% S, 9% R |

EXAMPLE 6

Transformation of the ethyl ester of racemic naproxen into S-naproxen by Bacillus Species In IV-8 grown in a fermenter The same procedure as described in example 5 was conducted with the Bacillus species In IV-8. Samples were taking during the 70 hours incubation period and assayed as described before during that period the dry weight as well as the volumetric activity remained substantially constant. The pH value changed during that period from 6.4 to 7.9 in the skimmed milk culture and from 6.2 to 8.4 in the enriched skimmed milk culture.

The results are summarized in Table 6.

TABLE 6

Results of the fermentation of the Bacillus species In IV-8 using skimmed milk and enriched skimmed milk respectively.

|  | culture using skimmed milk | culture using skimmed milk enriched with PSI PSIII and lactate |
|---|---|---|
| Dry weight | 0.7 g/l | 2.5 g/l |
| Volumetric activity | 10 mg Naproxen formed/l/hr | 25 mg Naproxen formed/l/hr |
| Enantiomeric distribution | 94% S, 6% R | not determined |

EXAMPLE 7

Transformation of the ethyl ester of R,S-ibuprofen into S-ibuprofen with different micro-organisms All tests were performed with 25-100 ml medium in 100-500 ml baffle flasks, as described in examples 1 and 2. The media were inoculated from cultures pregrown for 24 hours in a rich complex medium (e.g. BHI) and grown for 48 hours. Thereafter depending on the culture volume, 20 or 80μl ethyl ester of racemic ibuprofen was added to the cultures and incubated for 24 hours.

The cultures were extracted with $CH_2Cl_2$ after acidification to pH 2.5 with $H_3PO_4$ and the addition of a small amount of ammonium sulphate. The ibuprofen present in the extracts was derivatized into a naphthalene-methylamide derivative in order to determine its enantiomeric purity.

To 3 ml extract 200, μl of a solution of 2-bromo-1-methylpyridin iodide dissolved dimethylformamide (50 mg/ml) and 200μl of a solution of 1-naphthalene-methylamine dissolved in $CH_2Cl_2$ (100 mg/ml) were added and allowed to react for 5 minutes at 22° C. The reaction mixture was dried under N2 at 60° C. The remaining residue was dissolved in 3 ml isooctane/$CH_2Cl_2$ (2:1 v/v) and extracted after the addition of 2 ml 1 N $H_2SO_4$.

The organic layer was analyzed on HPLC using a chiral DNBPG column eluted with isooctane/isopropylalcohol/methanol (97/2/1 v/v) or in cases in which impurities disturbed the analysis with isooctane/isopropylalcohol/methanol (98/1/1 v/v).

Results are presented in Table 7.

TABLE 7

| Microorganism | Ibuprofen formed mg/culture | % S | % R | culture volume (ml) |
|---|---|---|---|---|
| Arthrobacter paraffineus ATCC 21218 | 9.8 | 85 | 15 | 25 |
| Bacillus licheniformis* ATCC 11945 | 0.8 | 99 | 1 | 25 |

TABLE 7-continued

| Microorganism | Ibuprofen formed mg/culture | % S | % R | culture volume (ml) |
|---|---|---|---|---|
| Bacillus subtilis In IV-8* CBS 680.85 | 0.4 | 89 | 11 | 25 |
| Bacillus subtilis Nap 10-M CBS 805.85 | 1.4 | 92 | 8 | 25 |
| Bacillus subtilis Sp III-4 CBS 806.86 | 4.2 | 88 | 12 | 25 |
| Bacillus subtilis Thai I-8 CBS 679.85 | 4.3 | 96 | 4 | 25 |
| Mucor angulimacrosporus IAM 6149 | 4.3 | 96 | 4 | 25 |
| Pseudomonas aeruginosa IFO 13130 | 5.5 | 81 | 9 | 25 |
| Pseudomonas fluorescens IFO 3081 | 3.4 | ≧95 | ≦5 | 25 |
| Pseudomonas fluorescens Kor I-6/CBS 807.85 | 3.9 | 94 | 6 | 100 |
| Pseudomonas ovalis IAM 1049 | 1.6 | 98 | 2 | 100 |
| Pseudomonas putida IFO 12996 | 1.6 | ≧95 | ≦5 | 25 |
| Pseudomonas riboflavina IFO 13584 | 0.7 | 98 | 2 | 100 |
| Streptomyces flavovirens IFO 3412 | 0.6 | ≧95 | ≦5 | 25 |
| strain is III-25 CBS 666.86 | 1.0 | 82 | 18 | 100 |
| strain LK 3-4 CBS 667.86 | 0.4 | ≧95 | ≦5 | 25 |
| strain Sp 4 CBS 668.86 | 0.9 | 95 | 5 | 25 |
| strain Thai III 18-1 CBS 669.86 | 7.0 | 87 | 13 | 25 |
| strain Thai VI 12 CBS 670.86 | 8.6 | 97 | 3 | 25 |

The values presented are the mean from experiments performed in duplicate. With the micro-organisms indicated with a * these values were obtained from a single experiment. In this case only 10 μl ibuprofen dissolved in 50 μl tetradecane was added to the cultures.

EXAMPLE 8

Transformation of the methyl ester of S-ibuprofen into S-ibuprofen with different micro-organisms All tests were performed as described in Example 7. Instead of the ethyl ester of racemic ibuprofen, the methyl ester of racemic ibuprofen was added to the cultures.

Results are presented in Table 8.

TABLE 8

| Microorganism | Ibuprofen formed mg/culture | % S | % R | culture volume (ml) |
|---|---|---|---|---|
| Arthrobacter paraffineus ATCC 21218 | 9.1 | 87 | 15 | 25 |
| Bacillus licheniformis* ATCC 11945 | 1.5 | 99 | 1 | 25 |
| Bacillus subtilis In IV-8* CBS 680.85 | 0.5 | 90 | 10 | 25 |
| Bacillus subtilis Nap 10-M CBS 805.85 | 2.2 | 93 | 7 | 25 |
| Bacillus subtilis Sp III-4 CBS 806.86 | 5.5 | 89 | 11 | 25 |
| Bacillus subtilis Thai I-8 CBS 679.85 | 5.7 | 97 | 3 | 25 |
| Mucor angulimacrosporus IAM 6149 | 6.1 | 93 | 7 | 25 |
| Pseudomonas fluorescens IFO 3081 | 3.1 | 93 | 7 | 25 |
| Pseudomonas putida IFO 12996 | 0.7 | ≧95 | ≦5 | 25 |
| Pseudomonas riboflavina IFO 13584 | 1.3 | 88 | 12 | 25 |
| Streptomyces flavovirens | 0.2 | ≧95 | ≦5 | 25 |

TABLE 8-continued

| Microorganism | Ibuprofen formed mg/culture | % S | % R | culture volume (ml) |
|---|---|---|---|---|
| IFO 3412 strain LK 3-4 CBS 667.86 | 0.2 | ≧95 | ≦5 | 25 |
| strain Thai III 18-1 CBS 669.86 | 3.1 | 88 | 12 | 25 |
| strain Thai VI 12 CBS 670.86 | 4.0 | ≧93 | ≦7 | 25 |

The values presented are the mean from experiments performed in duplicate. With the micro-organisms indicated with * these values were obtained from a single experiments. In this case only 10 μl ibuprofen dissolved in 50 μl tetradecane was added to the cultures.

EXAMPLE 9

Characterization of the naproxen methyl esterase present in Bacillus subtilis Thai I-8 (CBS 679.85)

Bacillus Thai I-8 was grown in an Eschweiler fermenter containing 10% skimmed milk (see example 5).

After 28 hours growth the cells were collected by centrifugation. The cells were solved in 0.1 M Tris HCl pH 8.0 and treated with lysosym (0.5 mg/ml lysosym, 4 mg/ml EDTA) for 18 hours at room temperature followed by DN'ase treatment (0.01 mg/ml DN'ase, 3.5 mg/ml $MgCl_2$) for one hour at the same temperature.

After centrifugation the protein part of the supernatant was precipitated at 70% ammoniumsulphate saturation. After centrifugation the pellet was solved in 0.01 M MOPS (3-(N-morpholino)propanesulfonic acid) buffer pH 7.5 and dialysed for 18 hours against the same buffer containing 0.02% $NaN_3$ as preservative.

The final solution was analyzed on a preparative HPLCS-EC (size-exclusion chromatography) column (TSK 2000 SW, 600×21.5 mm) eluted with 0.1 M sodium acetate pH 5.5 at a flow rate of 6 ml/min. From 10 minutes on column fractions of 2 ml were collected and tested for the presence of lipase and S-naproxen methyl esterase activity.

The lipase activity was assayed in 0.1 M MOPS pH 7.5 with 1 mg/ml p-nitrophenyllaureate as substrate. The lipase activity, which corresponds to the formation of p-nitrophenol, can be measured at 405 nm.

The S-naproxen methyl esterase was assayed in 0.1 M MOPS pH 8.0 with 20 mg of S-naproxen methyl ester/ml. After 18 hours incubation the amount of S-naproxen formed was measured by HPLC as described in example 2.

FIG. 1 shows the HPLCS-EC profile of the Bacillus Thai I-8 cell lysate. The S-naproxen methyl esterase (fraction 37) is clearly separated from the lipase activity (fraction 31) present in this micro-organism.

In Table 9 the enantiomeric selectivity of the cell lysate and fraction 31 and 38 of the HPLCS-EC are compared. The esterase activity on R and S-naproxen methyl ester were tested in the same way as described above.

The apparent molecular weight of the protein fraction containing the S-naproxen esterase activity was estimated using a protein mixture of known molecular weights as standard to be 27000.

Figure 2:
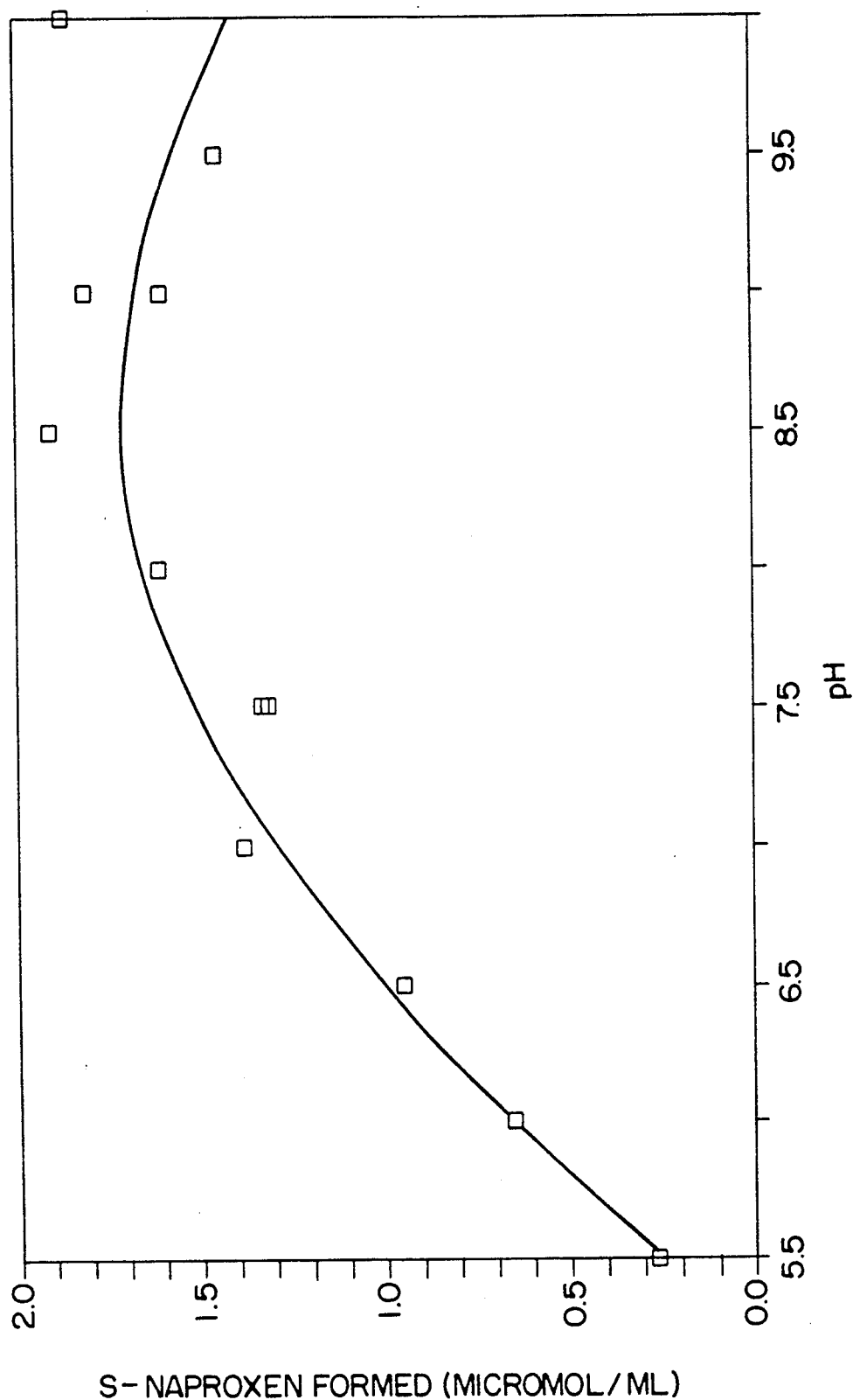

The pH dependence of the hydrolysis of S-naproxen methyl ester under the assay conditions is shown in FIG. 2. The buffers used were 0.1 M phosphoric acid (pH region 5.5-7.5), 0.1 M Tris-HCl (pH region 7.5-9.0) and 0.1 M glycine (pH region 9.0-10.0).

Figure 3:
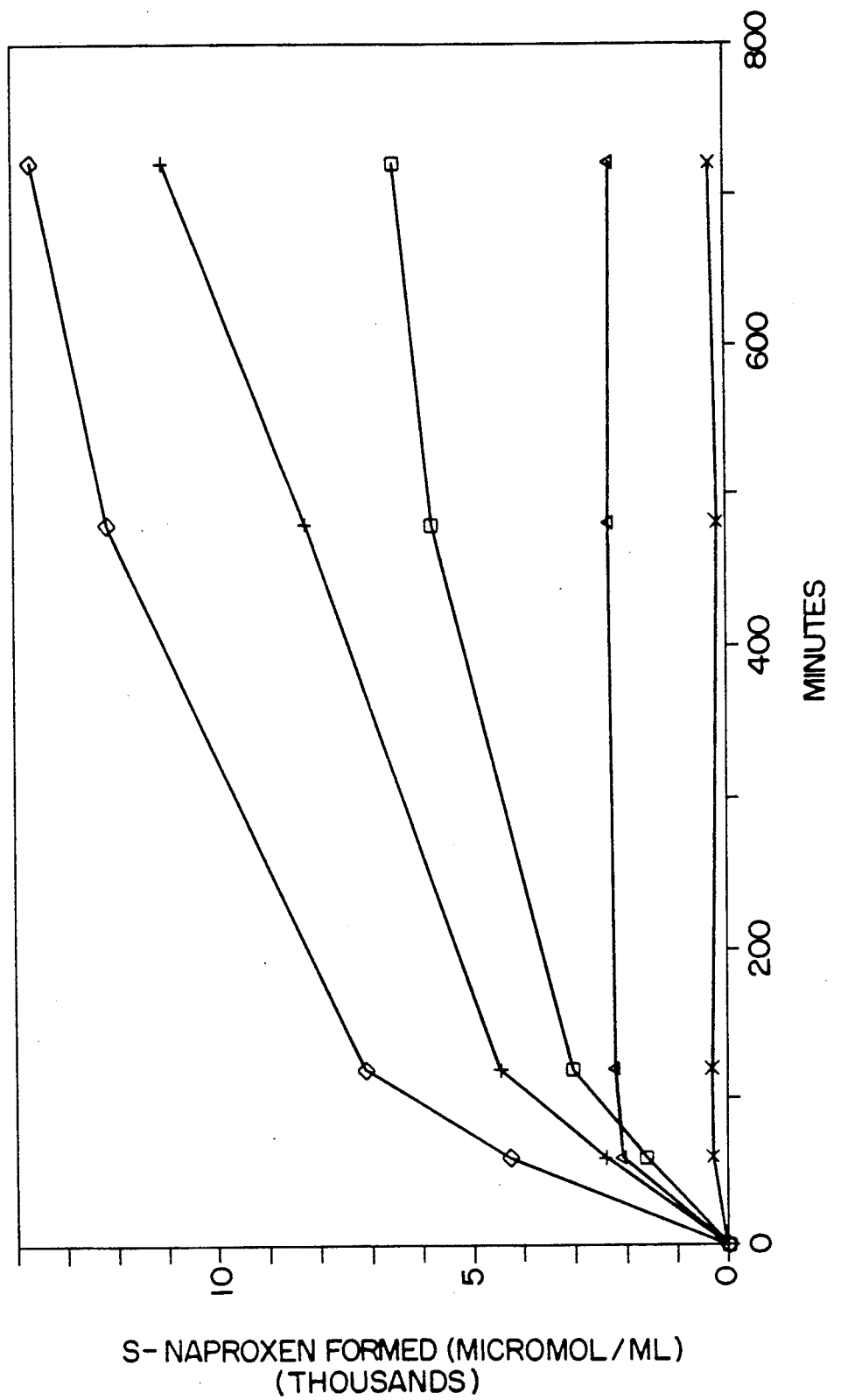

The influence of the temperature on the esterase reaction is shown in FIG. 3.

At a temperature above 45° C. hardly any enzymatic hydrolysis is found. The hydrolysis at 37° C. is roughly two times higher than at 25° C.

TABLE 9

| | Enzyme activity | S-naproxen formed from S-ester (mM) | R-naproxen formed from R-ester (mM) | S-specificity (%) |
|---|---|---|---|---|
| Thai cell-lysate | | 2.891 | 0.087 | 97.1 |
| fraction 31 | "lipase" | 0.090 | 0.119 | 43.1 |
| fraction 38 | "esterase" | 5.264 | 0.064 | 98.8 |

EXAMPLE 10

Molecular cloning of the gene responsible for the stereoselective conversion of RS- Naproxenester A plasmid, pNAPT-2, containing a chromosomal DNA fragment of Bacillus subtilis Thai I-8 CBS 679.85) was prepared as described below.

General cloning techniques have been used as described in the handbook of T. Maniatis et al., 1982, Molecular Cloning, Could Spring Harbor Laboratory. All DNA modifying enzymes were obtained from commercial suppliers and they were used according to the manufacturers' instructions. Materials and apparatus for DNA separation and purification were used according to instructions from the supplier.

The positive selection vector pUN121 (Nilsson et al., 1983, Nucleic Acids Res. 11, p. 8019) was used. This vector carries an ampicillin resistance gene, a tetracyclin resistance gene and a C1-repressor gene. Transcription of the tetracyclin gene is prevented by the gene product of the $C_1$-repressor gene. Insertion of foreign DNA into the Bcl 1 site of the $C_1$-repressor gene results in activation of the tetracyclin gene. This allows a positive selection of recombinants on ampicillin/tetracyclin agar plates.

Partially Sau3A digested Bacillus subtilis Thai 1-8 DNA was mixed with Bcl 1 digested pUN121 DNA. After recirculization by the use of polynucleotide ligase, the DNA mixture was introduced into E. coli DH1(ATCC 33849) using the $CaCl_2$ transformation procedure as described (T. Maniatis et al., 1982).

1000 E. coli colonies were obtained which were resistant to ampicillin and tetracyclin. All transformants were stored and replica-plated according to J. P. Gergen et al. (Nucleic Acids Res. 7, p. 2115, 1979). Replicated colonies were screened using a soft agar overlay technique based on a previously described procedure to detect esterase activity (T.B. Higerd and J. Spizizen, 1973, J. Bacteriol. 114, p. 1184). Essentially a mixture of 0.5% low-melting agarose, 0.5 M potassiumphosphate (pH 7.5), 0.5 mg/l beta-naphthyl acetate and 0.5 mg/ml fast-blue is spread over the transformants. Within a few minutes colonies with esterase or lipase activity color purple. Such colonies were grown overnight in 2×YT (16 g/l Bactotryptone, 10 g/l Yeast Extract, 5 g/l NaCl) medium and subsequently assayed for their ability to convert S-naproxen ester to S-naproxen (method of example 1). One E. coli transformant was able to convert S-naproxen ester. The plasmid isolated from this transformant, which was called pNAPT-2, is designated in FIG. 4. Its size is 9.4 kb.

The activity of E. coli/pNAPT-2 and E. coli/pNAPT-7 (assayed according to Example 12) grown overnight in 2x YT medium is shown in Table 10. E. coli cells with only plasmid pUN121 were unable to hydrolyse S or R-naproxen ester. This proves that all information needed for S-naproxen hydrolyzes resides in the 5 kb Bacillus subtilis Thai I-8 DNA insert.

A sample of E. coli DH1 carrying plasmid pNAPT-2 has been deposited with CBS under accession number 671.86).

TABLE 10

|  | Activity (u/l) | S-specificity (%) |
|---|---|---|
| E. coli/pUN 121 | 0 | — |
| E. coli/pNAPT-2 | 45 | >95 |
| E. coli/pNAPT-7 | 761 | 99.4 |

EXAMPLE 11

Improvement of esterase activity by introducing multiple gene copies in Bacillus subtilis The esterase-encoding plasmid pNAPT-2 carries a 5 kb Bacillus subtilis Thai I-8 (CBS 679.85) DNA insert. Since this is much more than the minimum size expected for a gene encoding a protein of around 30 kb it is conceivable that the insert might be shortened without losing esterase activity. To test for this possibility Hind III restriction enzyme fragments of pNAPT-2 were ligated into pPNeo/ori. This was performed as described below. pPNeo/ori was constructed by ligating the 2.7 kb $EcoR_1S$-ma 1 restriction fragment of $pUC_{19}$, (C. Yanisch-Perron et al., Gene 33, p. 103, 1985) to the 2.5 kb $EcoR_1S$-naB1 restriction fragment of pUB110 (T.C. Gryczan et al., J. Bacteriol., 134, p. 318, 1978). The resulting shuttle plasmid, pPNeo/ori (5.2 kb) has the capacity to replicate both in E. coli and in Bacillus species due to the presence of the $pUC_{19}$ origin, and the pUB110 origin. In addition pPNeo/ori carries a gene encoding ampicillin resistance and a gene encoding neomycin resistance (C. Yanisch-Perron et al., 1985; M. Matsumura et al., J. Bacteriol., 160, p. 413, 1984).

For subcloning Hind III digested pNAPT-2 was mixed with Hind III digested pPNeo/ori and ligated. The mixture was transformed to E. coli JM101 hsds as described (Maniatis et al., 1982). E. coli JM101 hsds was obtained from the Phabagen collection (accession number PC 2493 Utrecht, The Netherlands). Colonies capable of hydrolyzing beta-naphthyl acetate were selected as described in example 10. From two positive colonies, plasmid DNA was isolated and characterized in detail by determining several restriction enzyme recognition positions. The physical maps of these plasmids, pNAPT-7 and pNAPT-8, are given in FIG. 5 and 6. The activity of E. coli/pNAPT-7 ani E. coli/pNAPT-8 towards S-naproxen methyl ester was determined (Table 11).

It can be seen that both plasmids carry the 2.2 kb Hind III-Hind III fragments of pNAPT-2 as their insert, albeit that their orientations are opposite. It also appears that the gene for the esterase must be located within their 2.0 kb portion of Thai I-8 DNA.

After extraction from E. coli JM101 hsds the plasmids pNAPT-7 and pNAPT-8 were transformed to protoplasts of Bacillus subtilis 1-85 and Bacillus subtilis 1 A-40 (S. Chang and S.N. Cohen, Mol. Gene Genet. 168, p.111, 1979). Bacillus subtilis 1-85 (Yuki, S., 1967, Jpn. J. Genet. 42, p. 251) and Bacillus subtilis 1A40 (Bacillus Stock Center B.G.S.C. 1A40) have been described.

Neomycin resistant colonies were tested for their ability to hydrolyze S-naproxen methyl ester after fermentation in 2×YT broth according to the method described (see Example 12). In Table 11 the activities are shown. It can be seen that the improvement achieved by the introduction of multiple gene copies is about 300 fold. Hence, the suitability of the microorganisms and of the substances derived therefrom, for use in a process to hydrolyze S-naproxen ester is highly improved.

Although it is known that gene cloning can improve the expression level of an enzyme, the amount of enhancement in the case of esterase is very surprising. Very often problems as incorrect folding, protein degradation and intracellular precipitation are encountered when cloning the gene for an enzyme (Harris, T.J.R., 1983, Genetic Engineering 4, Academic Press). Unexpectedly none of these problems seems to occur when cloning esterase genes.

TABLE 11

|  | Activity (u/l) |
|---|---|
| E. coli JM101 hsds/pNAPT-7 (CBS 712.86 | 1064 |
| E. coli JM101 hsds/pNAPT-8 (CBS 672.86) | 1160 |
| Bacillus subtilis 1-85/pNAPT-7 (CBS 673.86) | 1011 |
| Bacillus subtilis 1A40/pNAPT-7 (CBS 675.86) | 965 |
| Bacillus subtilis 1A40/pNAPT-8 (CBS 674.86) | 1228 |
| E. coli JM101 hsds/pUN 121 | 0.0 |
| Bacillus subtilis 1-85 | 8.0 |
| Bacillus subtilis 1A40 (BGSC 1A40) | 0.0 |
| Bacillus subtilis Thai I-8 (CBS 679.85) | 3.5 |

EXAMPLE 12

Characterization of the naproxen methyl esterase of E. coli JM 101 hsds/pNAPT-7

One liter fermentation broth of E. coli JM 101 hsds/pNAPT-7 of example 11 was used. The broth was centrifuged. The pellet was suspended in 0.1 M Tris-HCl buffer pH 8.0 and incubated with 1 mg/ml lysosym, 4 mg/ml EDTA in the presence of 1% v/v octanol for 60 minutes at 30° C. The DNA j was hydrolyzed by 0.02 mg/ml DN'ase in the presence of 15 mM Mg2+(30 minutes at 22° C.).

After centrifugation the protein part of the supernatant was precipitated at 60% ammonium sulphate saturation. After centrifugation the pellet was solved in 10 mM MOPS pH 7.5 and 10 times concentrated by ultrafiltration (Amicon YM 10). The specific activity of the E. Coli pNAPT-7 retentate on the S-naproxen methyl ester (assayed in 0.1 M MOPS pH 7.5 at 25° C. in the presence of 20 mg S-naproxen methyl ester per ml, 2% Tween, 1 mg/ml BSA (Bovine Serum Albumin) was found to be 1.6 Units per mg protein. Through the whole specification 1 Unit (u) is defined as the amount of enzyme that hydrolyzes $1 \times 10^{-6}$ mol S-naproxen methyl ester per minute under the specified conditions. Tween is added for the improvement of the solubility of the strongly hydrophobic ester and BSA to avoid the inactivation of the enzyme by aspecific adsorption. The protein concentration was determined according to Bradford with BSA as standard.

The E. coli pNAPT-7 retentate after ultrafiltration was analyzed on the HPLCS-EC system described in Example 9.

From 15 minutes on column fractions of 2 ml were collected and tested for S-naproxen esterase activity (see Example 9).

Figure 7:
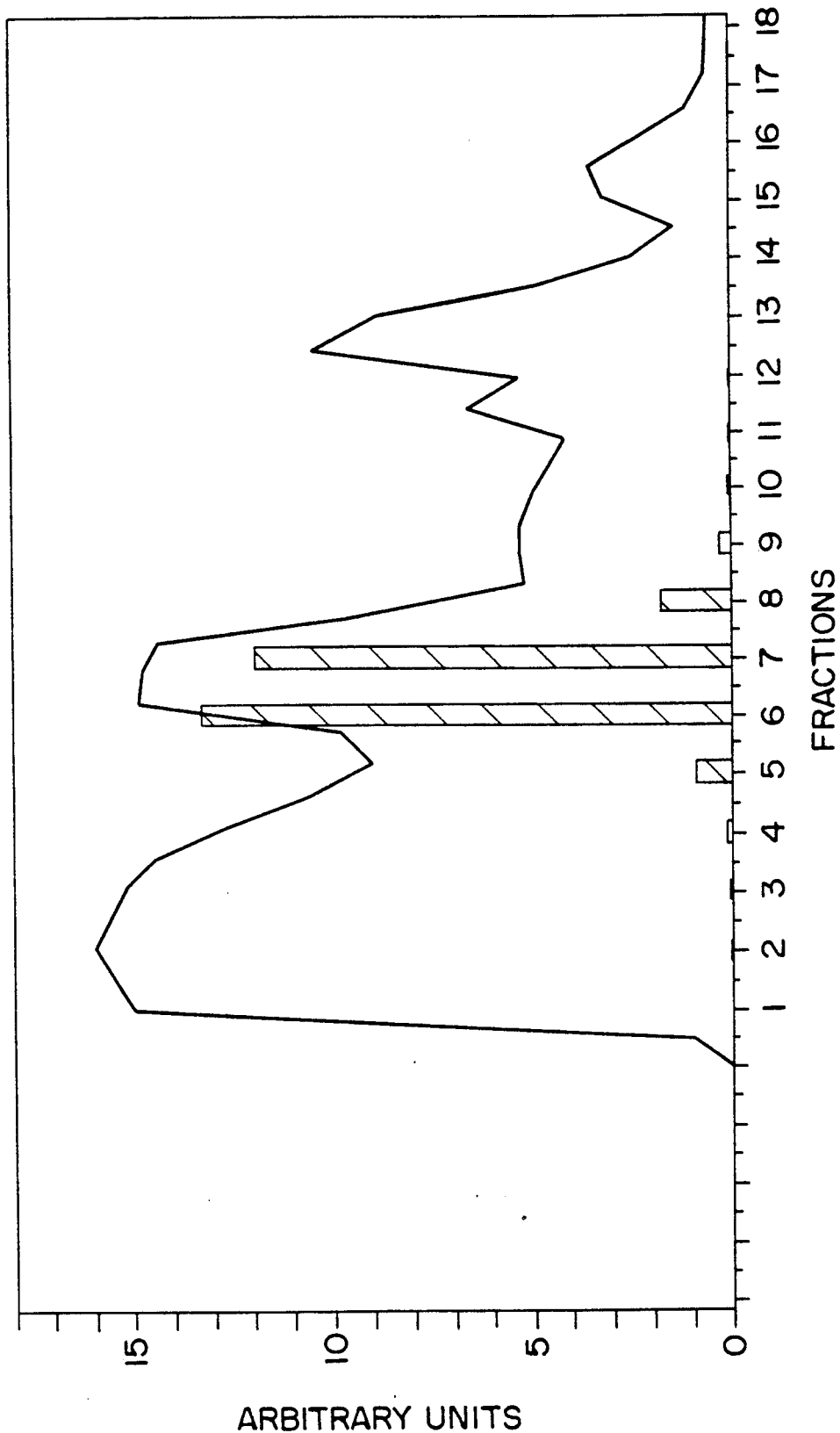

FIG. 7 shows the OD-280 nm absorbance and the esterase activity of the HPLCS-EC fractions. The S-naproxen esterase activity (fraction 26) coincides with a peak in the absorbance profile eluting. The retention time of the Bacillus subtilis Thai I-8 esterase analyzed in exactly the same manner was the same (results not shown).

Figure 8:
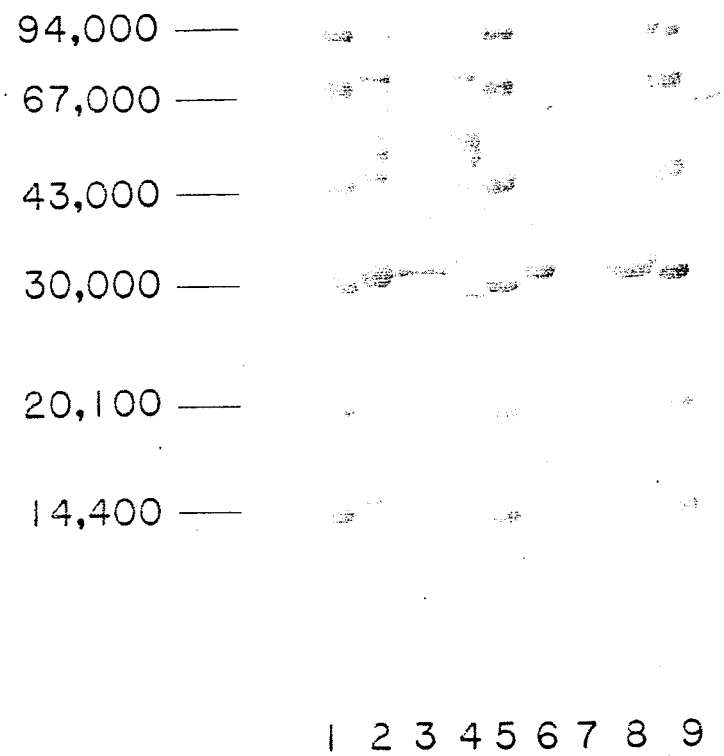

FIG. 8 shows a 12.6% SDS-PAGE according to Laemmli of the E. coli pNAPT-7 retentate and of fraction 26 of the HPLCS-EC.

Lahe 4 contains the E. coli JM 101 hsds/pUN 121. The PAGE (polyacrylamide gel electrophoresis) clearly shows that the most pronounced protein band in the E. coli pNAPT-7 retentate is the only protein band detectable in fraction 26 of the HPLCS-EC and absent in the E. coli.

FIG. 9 shows an isoelectricfocusing gel (LKB Ampholine PAG-plate, pH 3.5-9.5) of the E. coli pNAPT-7 retentate. In A the protein is stained with Serva Blue R. In B the esterase activity of the same samples is visualized by the β-naphthylacetate/FB (Fast Blue RR salt) method described in Example 10. It is shown that the most pronounced protein band in A appears to be responsible for the highest esterase activity.

EXAMPLE 13

Transformation of the ethyl ester of ibuprofen into ibuprofen by E. coli JM 101 hsds/pNAPT-7

The E. coli pNAPT-7 cell lysate after ammonium sulphate precipitation and ultrafiltration was tested on the hydrolysis of the ethyl ester of R and S-ibuprofen.

The enzyme activity was assayed at 25° C. in 0.1 MOPS buffer pH 7.5 with 0.3 mg of R or S-ibuprofen ethyl ester/ml, 2% Tween and 1 mg/ml BSA. After 2 hours incubation the reaction was stopped by the addition of acetonitrile.

The reaction mixture was analyzed on a HPLC-reversed phase column (Chrompack Polygosil 60D-10CN, 250×4.6 mm), eluted with 34% acetonitrile, 0.05 M phosphoric acid pH 3.0 at a flow rate of 1.5 ml/min. Retention times for R and S-ibuprofen and the ethyl ester of R and S-ibuprofen were 5.98 minutes and 11.08 minutes respectively. The results are summarized in Table 12.

The hydrolysis of the ethyl ester of S-ibuprofen is 60% of the hydrolyzing activity of the methyl ester of S-naproxen tested under the same conditions.

TABLE 12

| Substrate | ester group | u/l | S-specificity (%) |
|---|---|---|---|
| S-ibuprofen | ethyl | 39600 | 95.3 |
| R-ibuprofen | ethyl | 1865 | |
| S-naproxen | methyl | 65000 | |

EXAMPLE 14

Characterization of the S-naproxen esterase of Bacillus 1-85/pNAPT-7

Bacillus 1-85/pNAPT-7 was grown in a 5 liter Eschweiler fermenter in 2×TY medium.

The cell paste was isolated by centrifugation. The pellet was dissolved in 0.1 M Tris-HCl pH 8.0 and lyzed according to the method described in Example 9.

After centrifugation the supernatant was brought to 60% ammonium sulphate saturation and centrifuged again. The pellet was dissolved in 0.02 M MOPS pH 7.5 and ultrafiltrated using an Amicon YM10 filter. This cell lysate was analyzed on an analytical HPLCS-EC column (TSK 2000 SW, 2 times 300×7.5 mm), eluted with 0.01 M MES (2-(N-morpholino)ethane sulfonic acid) pH 5.6 and 0.1 M NaCl. Flow rate 1 ml/min. From 10 minutes on 1 ml fractions of the column eluate were collected and tested for S-naproxen methyl esterase activity using the method described in Example 12.

Figure 10:
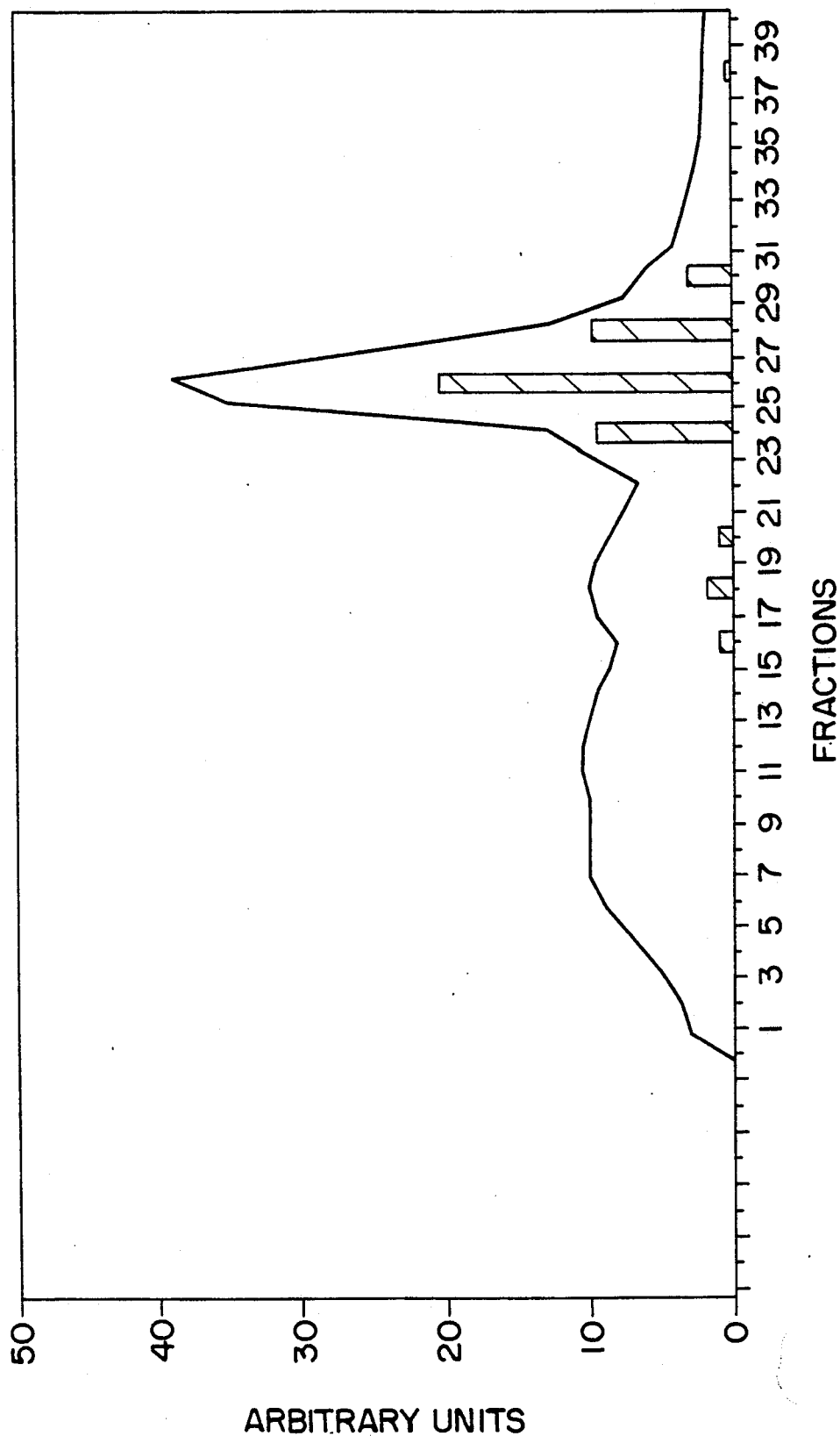

FIG. 10 shows the OD-280 nm profile and the esterase activity of the fractions. The retention time of the S-naproxen esterase corresponds to an apparent molecular weight of 27000. The specific activity of the different protein samples is summarized in Table 13. The esterase activity was assayed as described in Example 12.

The enantiomeric selectivity of the Bacillus pNAPT-7 retentate is shown in Table 14. The activity is assayed as described in Example 12.

In FIG. 8 12.6% SDS-PAGE according to Laemmli is shown of Bacillus pNAPT-7 and fraction 5 and 7 of the HPLCS-EC which represent respectively the lipase and S-naproxen esterase activities. The main protein band in the Bacillus retentate is the only protein present in fraction 7 and is absent is fraction 5 (lipase activity). The protein band in lane 8 corresponds to an apparent molecular weight of 31000.

In FIG. 9 an isoelectricfocusing gel is shown of Bacillus pNAPT-7 and fraction 7 (see for technical description Example 12). In the Bacillus pNAPT-7 retentate the lipase activity having an isoelectric point (IEP) of 4.5 is the dominating activity on the naphthylacetate substrate. In fraction 7 of the HPLCS-EC the main protein band has an IEP of 5.4 which coincides with the naphthylacetate hydrolyzing activity shown in part B. It must be noted that the β-naphthyl fast-blue assay reacts much more sensitive with a lipase than with an esterase.

The OD 280 nm peak (fraction 7) of the HPLCS-EC appears to contain the naproxen esterase and consists of one main protein band on SDS-PAGE. The isoelectricfocusing gel confirms that the main protein band of fraction 7 possesses the esterase activity. This means that the cloning of the esterase activity of Bacillus subtilis Thai I-8 both in E. coli and Bacillus results in a dramatic increase in esterase production. In fact the naproxen esterase in E. coli pNAPT-7 and Bacillus pNAPT-7 has become the protein with the highest concentration in the cell lysate of both micro-organisms.

TABLE 13

| Sample | u/ml | protein conc. (mg/ml) | u/mg protein |
|---|---|---|---|
| Bacillus 1-85/pNAPT-7* | 196 | 120 | 1.2 |
| fraction 6 HPLC-SEC | 6.7 | 1.1 | 6.1 |
| fraction 7 HPLC-SEC | 6 | 0.95 | 6.3 |
| Bacillus Thai I-8* | 0.221 | 107 | 0.002 |

*Cell lysate after lysis, ammonium sulfate precipitation and ultrafiltration.

TABLE 14

| | methyl ester added | u/ml | S-specificity (%) |
|---|---|---|---|
| Bacillus 1-85/ pNAPT-7 | S-naproxen | 105000 | 99.4 |
| | R-naproxen | 577 | |

Legends to the figures

FIG. 1 HPLC-SEC profile of the Bacillus Thai I-8 cell lysate

───────── : OD 280 nm

▨▨▨▨▨▨▨ : Lipase activity

▰▰▰▰▰▰▰ : naproxen methyl esterase activity

FIG. 2 The pH dependence of the hydrolysis of S-naproxen methyl ester under the assay conditions of Example 9.

Figure 4:
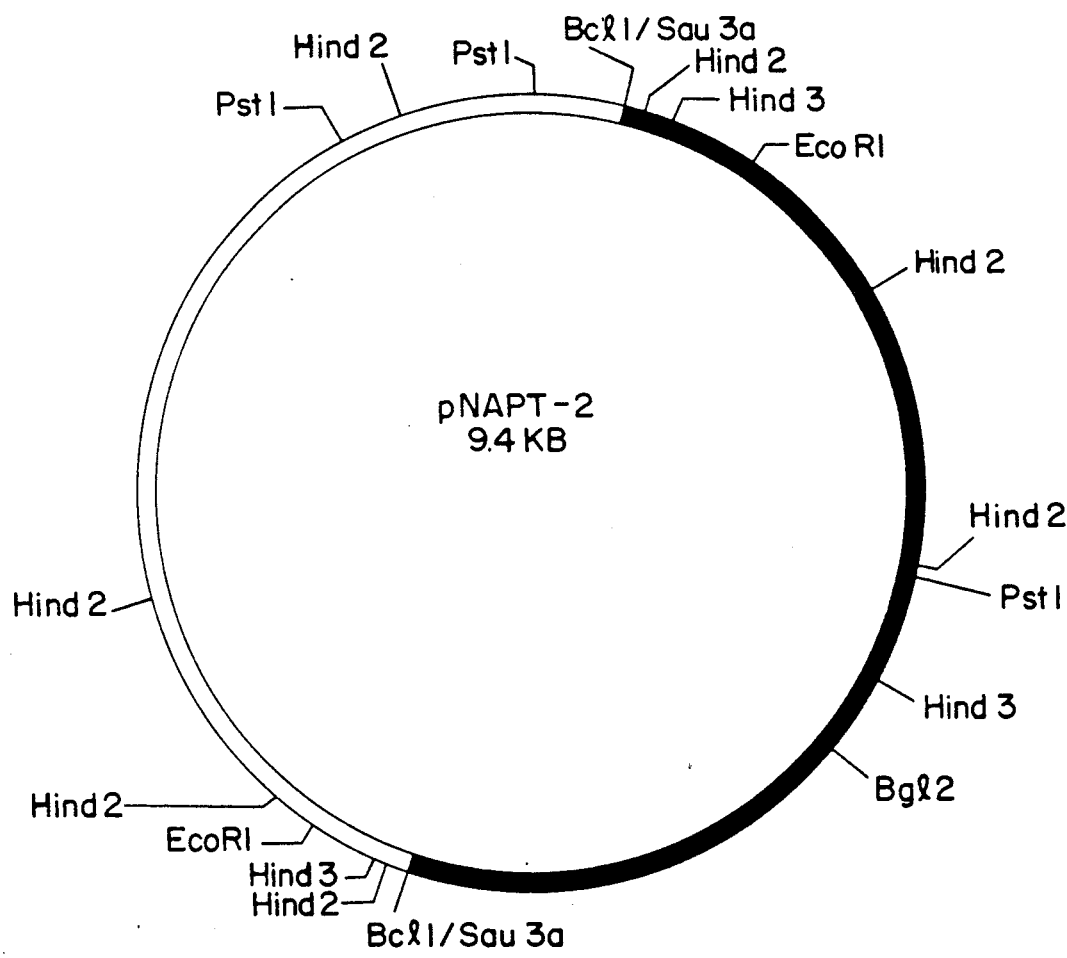

FIG. 3 The influence of the temperature on the esterase reaction $\square = 25° C., + = 30° C., \diamond = 37° C., \Delta = 45° C.$ and $\times = 60° C.$ FIG. 4 Restriction map of pNAPT-2

A number of restriction enzyme recognition sites have been determined in plasmid pNAPT2, which has a size of 9.4 kb.

☐ : puN 121 DNA

: Thai I-8 DNA insert

The position at which partially Sau3a digested Thai I-8 DNA was ligated to pUN 121 is indicated by Bcl1/Sau3a.

Figure 5:
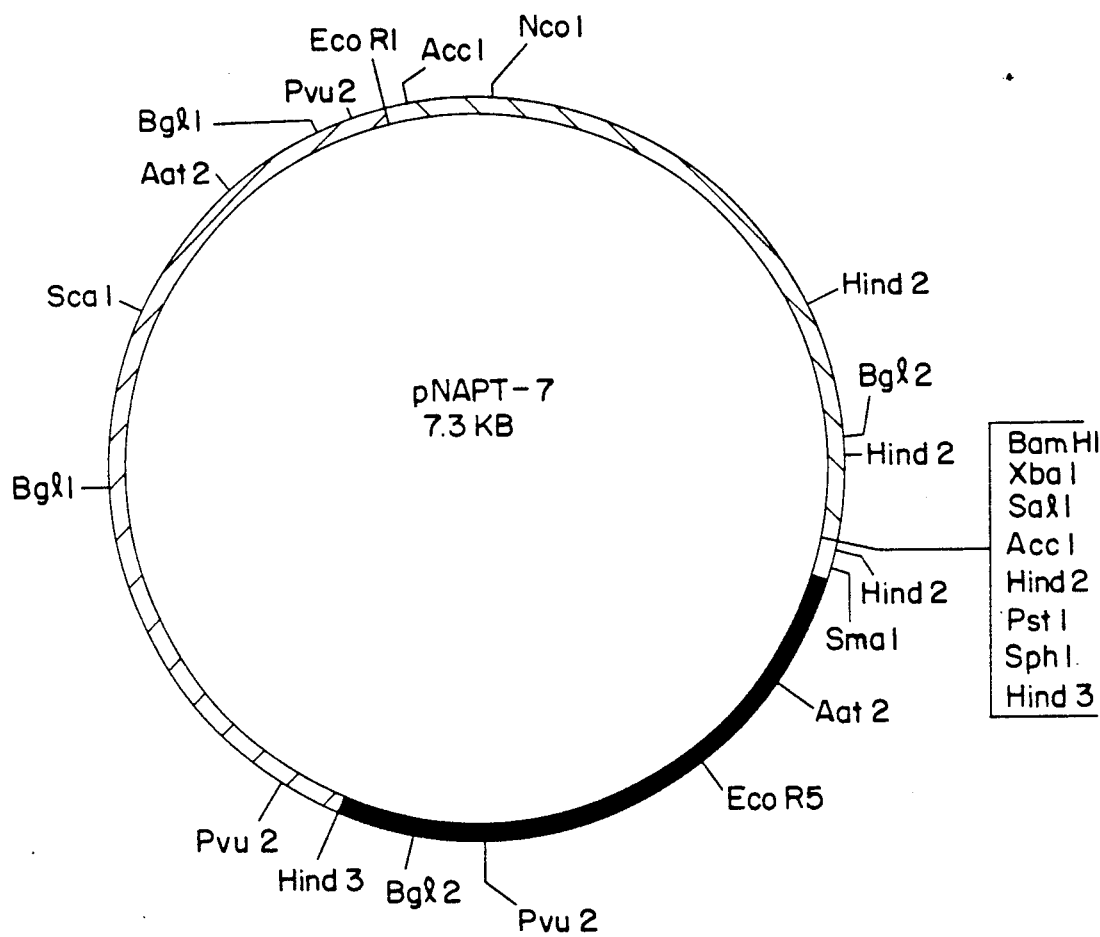
Figure 6:
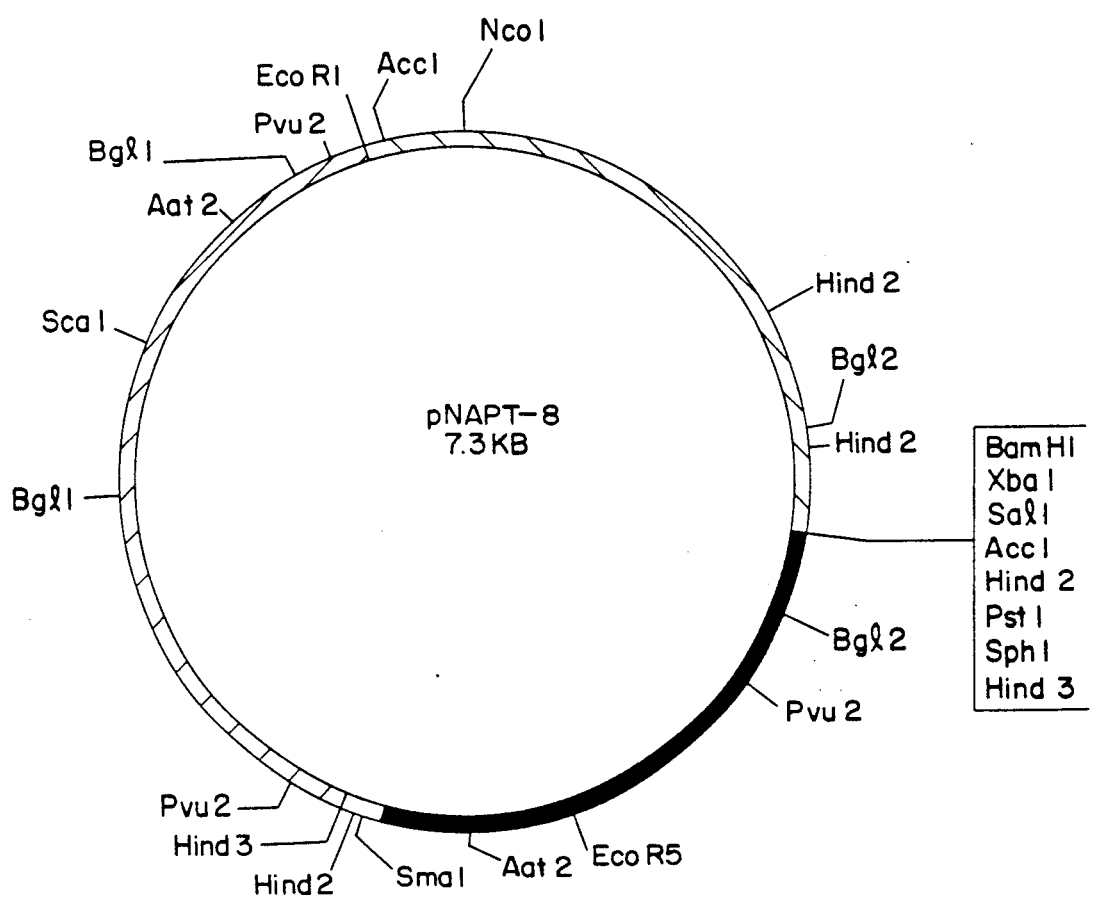

FIGS. 5 and 6. Restriction maps of pNAPT-7 and pNAPT-8, respectively

The 2.2 kb Hind III fragment of pNAPT-2 was cloned into pPNeo/ori. The resulting plasmids, pNAPT-7 and pNAPT-8, have been analyzed in detail with several restriction enzymes. Both plasmids have a size of 7.3 kb. It can be seen that pNAPT-8 carries the 2.2 Hind III fragment in an orientation opposite to that of pNAPT-7.

▰▰▰▰▰▰▰ : pUC 19 DNA

▨▨▨▨▨▨▨ : pUB 110 DNA

☐ : pUN 121 DNA

: Thai I-8 DNA

FIG. 7 The OD-280 nm adsorbance and the esterase activity of the HPLC-SEC fractions ▰▰▰▰▰▰▰ S-naproxen methyl esterase activity ───────── OD-280 nm FIG. 8 a 12.6% SDS-PAGE according to Laemmli of the E. coli pNAPT-7 retentate and of fraction 26 of the HPLC-SEC.

| Lanes 1, 5 and 9: | molecular weight markers |
|---|---|
| Lane 2: | E. coli pNAPT-7 retentate |
| Lane 3: | E. coli pNAPT-7 retentate after HPLC. gelfiltration, active fraction 26 |
| Lane 4: | E. coli/pUN 121 host strain |
| Lane 6: | Bacillus subtilis 1-85 with pNAPT-7 |
| Lanes 7 and 8: | Bacillus subtilis 1-85 with pNAPT-7 after HPLC gelfiltration, fraction 5 and 7 |
| Lane 10: | Bacillus Thai I-8 retentate. |

FIG. 9 An isoelectricfocusing gel (LKB Ampholine PAG-plate, pH 3.5-9.5) of the E. coli pNAPT-7 retentate
A. After staining with Serva Blue
B. After 62 -naphthylacetate/FBB staining
Lane 1: Marker proteins with known IEP
Lane 4: E. coli pNAPT-7 retentate
Lane 3: Bacillus subtilis 1-85 with pNAPT-7 retentate
Lane 2: as Lane 3 after HPLC gelfiltration, active fraction FIG. 10 The OD-280 nm profile and the esterase activity of the HPLC-SEC fractions ▰▰▰▰▰▰▰ S-naproxen methyl esterase activity ───────── OD-280 nm

We claim:

1. Microbial purified esterase having the ability for stereoselective hydrolysis of naproxen ester into naproxen having at least 99.4% by weight of the S-configuration, said esterase having a specific activity of at least 0.1 units per mg of esterase; an isoelectric point of 5.4; an apparent molecular weight of 31.000; a pH optimum between 6.5 and 10; and a temperature optimum between 30° and 45° C.

2. Esterase according to claim 1 wherein the ester residue of the naproxen ester is a substituted or unsubstituted alkyl group.

3. Esterase according to claim 1 being produced by a transformant which has obtained or has increased esterase activity by the introduction of at least one gene encoding for said esterase.

4. Esterase obtainable from micro-organisms selected from the group consisting of Bacillus species Thai I-8 (CBS 679.85); Bacillus species in IV-8 (CBS 680.850; Bacillus species Nap 10-M (CBS 805.85); Bacillus species Sp III-4 (CBS 806.85); Pseudomonas species for I-6 9CBS 807.85); Escherichia coli DH 1/pNAPT-2 (CBS 671.86); Escherichia coli JM01 hsds pNAPT-7 (CBS 712.86); Bacillus subtilis 1-85/pNAPT-7 (CBS 673.86); Bacillus subtilis 1A-40/pNAPT-7 (CBS 675.86); Bacillus subtilis 1A-40/pNAPT-8 (CBS 674.86); Escherichia coli JM hsds/pNAPT-8 (CBS 672.86); Strain LK 3-4 (CBS 667.86); Strain Sp 4 (CBS 668.86); Strain Thai III 18-1 (CBS 669.86); Strain Thai VI 12 (CBS 670.86); Strain is III-25 (CBS 666.86).

5. Enzyme according to claim 1 having a specific activity of at least 1 unit as hereinbefore defined.

* * * * *